US012685698B2

(12) United States Patent
Tardieu et al.

(10) Patent No.: US 12,685,698 B2
(45) Date of Patent: Jul. 21, 2026

(54) CAPSULES COMPRISING A PERFUME COMPOSITION FOR SINGLE-DOSE FRAGRANCING

(71) Applicant: V. MANE FILS, Le Bar-sur-Loup (FR)

(72) Inventors: Audrey Tardieu, Grasse (FR); Jean-Michel Hannetel, Grasse (FR)

(73) Assignee: V. MANE FILS, Le Bar-sur-Loup (FR)

( * ) Notice: Subject to any disclaimer, the term of this patent is extended or adjusted under 35 U.S.C. 154(b) by 765 days.

(21) Appl. No.: 18/016,697

(22) PCT Filed: Jul. 19, 2021

(86) PCT No.: PCT/FR2021/051346
§ 371 (c)(1),
(2) Date: Jan. 18, 2023

(87) PCT Pub. No.: WO2022/018372
PCT Pub. Date: Jan. 27, 2022

(65) Prior Publication Data
US 2024/0082120 A1      Mar. 14, 2024

(30) Foreign Application Priority Data
Jul. 20, 2020    (FR) ..................................... 2007630

(51) Int. Cl.
| | |
|---|---|
| *A61K 8/11* | (2006.01) |
| *A61K 8/37* | (2006.01) |
| *A61K 8/73* | (2006.01) |
| *A61K 8/891* | (2006.01) |
| *A61Q 13/00* | (2006.01) |

(52) U.S. Cl.
CPC .................. *A61K 8/11* (2013.01); *A61K 8/37* (2013.01); *A61K 8/891* (2013.01); *A61Q 13/00* (2013.01)

(58) Field of Classification Search
CPC . A61K 8/37; A61K 8/73; A61K 8/891; A61K 8/11; A61Q 13/00
USPC ....................................................... 512/4, 1
See application file for complete search history.

(56) References Cited

U.S. PATENT DOCUMENTS

| | | |
|---|---|---|
| 5,670,159 A | 9/1997 | Morton et al. |
| 6,099,858 A | 8/2000 | Morton et al. |
| 2002/0078274 A1 | 6/2002 | Kutaragi et al. |
| 2009/0208568 A1 | 8/2009 | Hannetel et al. |
| 2010/0104613 A1 | 4/2010 | Chan et al. |
| 2016/0106637 A1 | 4/2016 | Shoji et al. |
| 2024/0082120 A1 | 3/2024 | Tardieu et al. |

FOREIGN PATENT DOCUMENTS

| | | | |
|---|---|---|---|
| CN | 105362092 | 3/2016 | |
| EP | 0 513 603 | 11/1992 | |
| EP | 1533364 | 5/2005 | |
| FR | 3042690 | 4/2017 | |
| KR | 20080016889 A | * 2/2008 | ........... A61K 9/4833 |
| KR | 10-2008-0016889 | 8/2014 | |
| PL | 0914385 8 | 10/2015 | |
| WO | WO-9509604 | 4/1995 | |
| WO | WO 2007/012981 | 2/2007 | |
| WO | WO 2012/089819 | 7/2012 | |
| WO | WO-2015/104436 | 7/2015 | |

OTHER PUBLICATIONS

Hartmann et al, KR 1020080016889 Machine Translation, Feb. 22, 2008 (Year: 2008).*
Official Action dated Sep. 3, 2025 in South Korean Application No. 10-2023-7005886.
The Wikipedia Ginkgo Semen Ethanol website, 에탄올 - 위키백과 , 우리 모두의 백과사전, , cited in Official Action dated Sep. 3, 2025 in South Korean Application No. 10-2023-7005886.
Search Report in Chinese Application No. 2021800630485.
First Office Action dated Apr. 10, 2024 in Chinese Application No. 2021800630485.
International Search Report for PCT/FR 2021/051346 dated Nov. 23, 2021.
Office Action dated Jul. 19, 2021 in Brazilian Application No. BR112023001031-4.
Office Action dated Oct. 12, 2024 in Chinese Application No. 2021800630485.
Office Action dated Apr. 1, 2025 in Japanese Application No. 2023-504204.
Office Action dated Jul. 10, 2024 in Russian Application No. 2023103357/04.
Second Office Action dated Dec. 17, 2024 in Russian Application No. 2023103357/04.

* cited by examiner

*Primary Examiner* — Jessica Whiteley
(74) *Attorney, Agent, or Firm* — B. Aaron Schulman; Stites & Harbison, PLLC

(57)      ABSTRACT

The invention relates to seamless capsule of core-shell type for fragrancing a user,
the shell comprising at least one hydrocolloid,
the core comprising at least one fragrancing agent and at least one lipophilic solvent,
characterized in that said shell is breakable, and in that the core comprises between 15 and 40% by weight of fragrancing agents relative to the total weight of the core, and between 60 and 85% by weight of a non-glyceride lipophilic solvent relative to the total weight of the core, said solvent being miscible with ethanol and having:
a viscosity of less than 10 mPa·s as measured at a temperature of 25° C. and at a shear rate of 10 s$^{-1}$;
a specific gravity of between 0.82 and 0.99; and
a spreading value greater than 850 mm$^2$/10 min.

14 Claims, 9 Drawing Sheets

[Fig. 1]
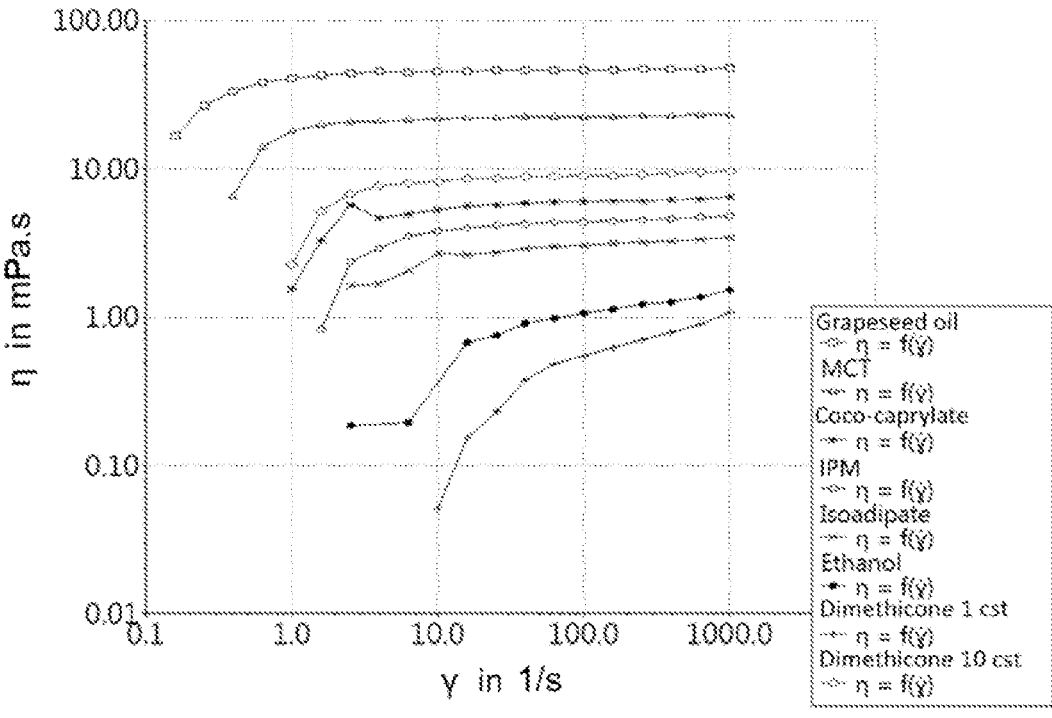
[Fig. 2]
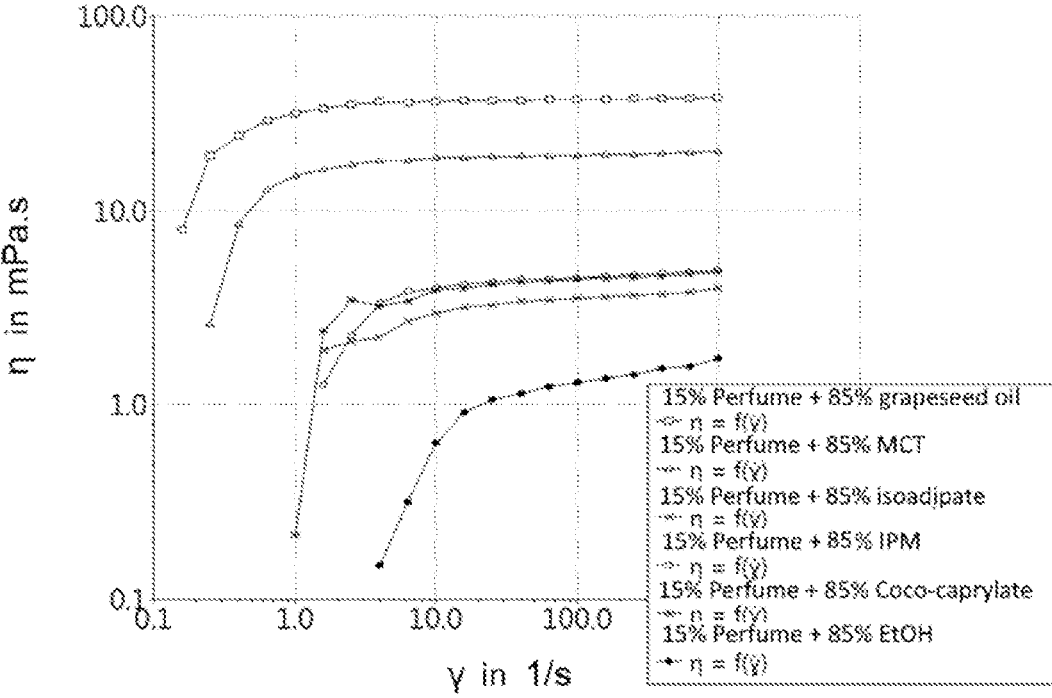

Viscosity with shear rate at 10 s-1, 25 ˚C

| | |
|---|---|
| ** | Significant greasy appearance |
| * | Greasy appearance |
| | No greasy appearance |
| ( ) | Greasy appearance not tested |

[Fig. 4]
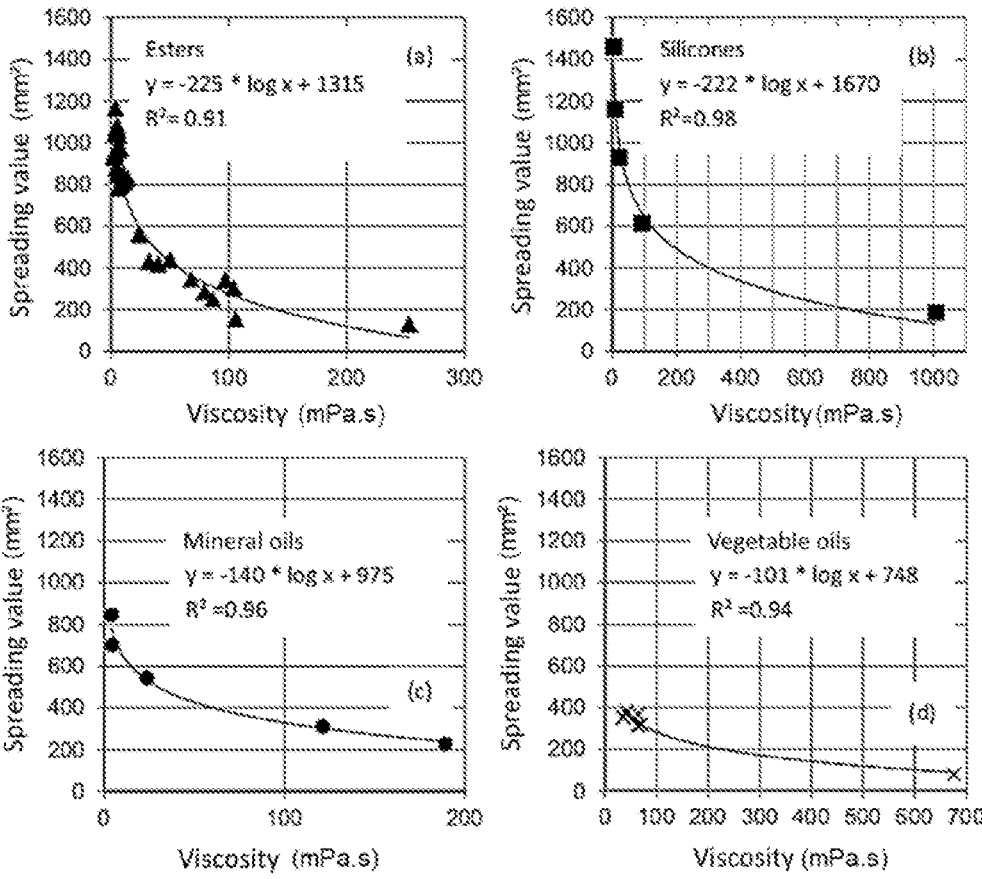
[Fig. 5]
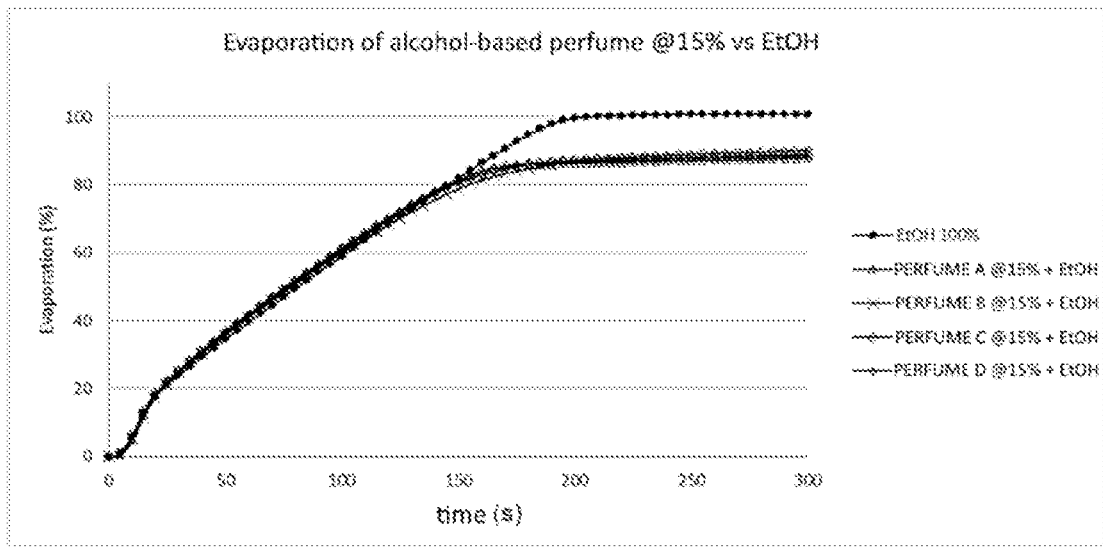

Pure Samples

CAPSULES COMPRISING A PERFUME COMPOSITION FOR SINGLE-DOSE FRAGRANCING

This invention relates to a dry and breakable capsule comprising a liquid perfume core, said capsule being intended for fragrancing, i.e. for the diffusion of fragrant molecules. After breaking, said capsule allows the user to fragrance themselves on the go and in an unconventional manner or to apply fragrant molecules without a greasy feeling when it is used.

Currently, in traditional perfumery, there are different types of conventional formulations for alcohol-based spray perfume:

"eau de Cologne" (EdC) containing from 4% to 6% of concentrated perfume;

"eau de toilette" (EdT) which contains from 7 to 12% of concentrated perfume;

"eau de parfum" (EdP), which is more expensive, reaches a concentration of 12 to 20% of concentrated perfume;

"perfumes" or "extracts", for which the perfume concentration can reach 40% in the case of particularly prestigious perfumes.

It is common practice for consumers to spray their perfume by pressing one or more times on the perfume bottle (thus delivering between 50 and 200 µl of perfume), which allows misting the perfume solution in the form of fine droplets measuring a few microns, for application on the skin, hair, or clothing.

However, the perfume and cosmetics industries must constantly innovate in order to better meet the demands of these consumers. Indeed, a study conducted in February 2019 by the Applicant on women in France and in the United States concluded that 80% of consumers say they are ready to fragrance themselves with a product other than an alcoholic spray.

New fragrancing application styles must therefore be developed in order to satisfy consumers.

However, two essential points must be taken into account in these needs for innovation in new fragrancing rituals. Firstly, there are the technical issues such as the perfume wear time, its fragrance rendering, and an optimal sensoriality. Indeed, it is never easy to transpose the formula of an eau de toilette or an eau de parfum to another medium: it is often necessary to make readjustments, with the advantages and disadvantages posed by each option. On the other hand, consumers are increasingly looking for a natural approach and for compositions without risk to the skin; it is for this reason that they are increasingly turning to perfumes in the form of oils, creams, or even aqueous solutions. Indeed, ethanol, which is the main solvent for solubilizing aromatic compounds, has disadvantages such as its dermal-sensitizing, drying, and irritating effects on the skin.

Among the various existing dosage forms, encapsulation consists of enclosing a liquid substance in a capsule. Encapsulation allows protecting the substance contained in the capsule against interactions with the external environment, and transporting the substance of interest to the location where it will be released at the desired time.

Currently, there are "capsule" or related types of devices comprising compositions incorporating perfume in particular.

For example, patent application FR3042690 describes a device for encapsulating perfume samples, as well as a method for manufacturing such devices. Said device for encapsulating perfume samples comprises an outer core-shell made of flexible and fluidtight material, comprising a cavity in which is housed a "capsule", typically composed of a tubular body closed by fluidtight means. Preferably, the tubular body is thus made of glass, sealed closed by a stopper, and contains a perfume sample. For other liquids, in particular not containing alcohol, the tubular body of the capsule may alternatively be made of PMMA (polymethyl methacrylate), closed by an ABS (Acrylonitrile Butadiene Styrene) film. When the tubular body of said capsule containing a perfume sample breaks, the perfume is released to outside the core-shell, enabling the fragrance of the perfume released into the internal cavity of the device to diffuse to outside the device. However, this device does not describe a "capsule" obtained by conventional encapsulation technology. In addition, the device as described and comprising a pseudo "capsule" is not easy to implement, and includes complex chemical materials. Finally, it only finds use as a device for sampling perfume, not as a means of wearing perfume.

As for patent application WO2012/089819, it describes a perfume capsule comprising:

an internal phase formed of an oil-in-water type of emulsion, the oily composition comprising a fragrancing agent, and the continuous aqueous phase entirely encapsulating said drop(s) of the oily phase; and a gelled external phase comprising at least one polyelectrolyte in the gelled state, entirely encapsulating said internal phase at its periphery.

The external phase also includes surfactants that improve the formation and gelation of multiple drops during the encapsulation process. It should be noted that the capsules according to patent application WO2012/089819 are in fact capsules encapsulating droplets of oil-in-water emulsion. In addition, the presence of surfactants can be irritating to the skin when applying said capsules. Finally, the capsules obtained according to that document are intended to be integrated into a cosmetic composition in the presence of a dermatologically acceptable vehicle, and are therefore not intended to be used as is by a user.

Until now, no encapsulated fragrance device that can be used on the go has existed on the market. Indeed, the devices such as those described above relate to capsules or microcapsules, either integrated into a bottle because they must be kept in a humid environment, or integrated into a cosmetic composition, or do not allow actually applying as perfume because they are integrated into a medium such as a card or pouch for smelling and evaluating perfumes prior to purchase in spray form.

The present invention relates to a dry, seamless, breakable capsule comprising a shell enclosing a liquid perfume core, said capsule being intended to diffuse fragrant molecules to allow fragrancing one's self, on the skin in particular.

More specifically, the first object of the invention relates to a seamless capsule of core-shell type for fragrancing a user, the shell comprising at least one hydrocolloid;

the core comprising at least one fragrancing agent and at least one lipophilic solvent;

characterized in that said shell is breakable, and in that the core comprises from 15 to 40% by weight of fragrancing agents relative to the total weight of the core and from 60 to 85% by weight of a non-glyceride lipophilic solvent relative to the total weight of the core, said solvent being miscible with ethanol and having:

a viscosity of less than 10 mPa·s as measured at a temperature of 25° C. and at a shear rate of 10 s$^{-1}$;

a specific gravity of between 0.82 and 0.99; and a spreading value greater than 850 mm$^2$/10 min.

The second object of this application relates to a method for manufacturing a breakable capsule comprising a shell and a core, comprising the steps of:

(A) co-extrusion of a hydrophilic external liquid phase and a lipophilic internal liquid phase, the external liquid phase comprising at least from 4 to 95% by weight of a hydrocolloid relative to the dry weight of said external phase, the internal liquid phase comprising at least from 15 to 40% by weight of fragrancing agents relative to the total weight of the core, from 0 to 10% by weight of ethanol relative to the total weight of the core, and from 60 to 85% by weight of a lipophilic non-glyceride solvent relative to the total weight of the core, said solvent being miscible with ethanol and having:

a viscosity of less than 10 mPa·s as measured at a temperature of 25° C. and at a shear rate of 10 s$^{-1}$;
a specific gravity of between 0.82 and 0.99; and
a spreading value greater than 850 mm$^2$/10 min;

(B) solidification and/or gelation of the surface of the capsules thus obtained, by immersion in a cold bath at a temperature of between 1° and 20° C.;

(C) drying the capsules; and (D) collecting the capsules.

The third object of this application relates to the use of a capsule according to the invention to fragrance a user.

The fourth object of this application relates to a method for fragrancing a user using the capsule according to the invention, characterized in that it comprises the following steps:

gripping the capsule according to the invention between two of the user's fingers;

rupturing said capsule by the action of a pressure enabling said capsule to be broken between the two fingers;

applying the oily perfumed composition contained in the capsule to the skin.

BRIEF DESCRIPTION OF DRAWINGS

Other features, details, and advantages will become apparent upon reading the detailed description below, and upon analyzing the appended drawings, in which FIG. 1 describes the rheological profile at 25° C. of pure oils compared to that of ethanol.

FIG. 2 describes the rheological profile at 25° C. of 15/85 w/w perfume+oil mixtures compared to the one with ethanol.

FIG. 4 describes the evolution of the spreading value as a function of viscosity (measured at 25° C.) for all families of lipophilic solvents: (a) esters, (b) silicones, (c) mineral oils, and (d) vegetable oils.

FIG. 5 describes the evaporation profile of standard alcohol-based perfumes at 15% in ethanol.

Figure 3:
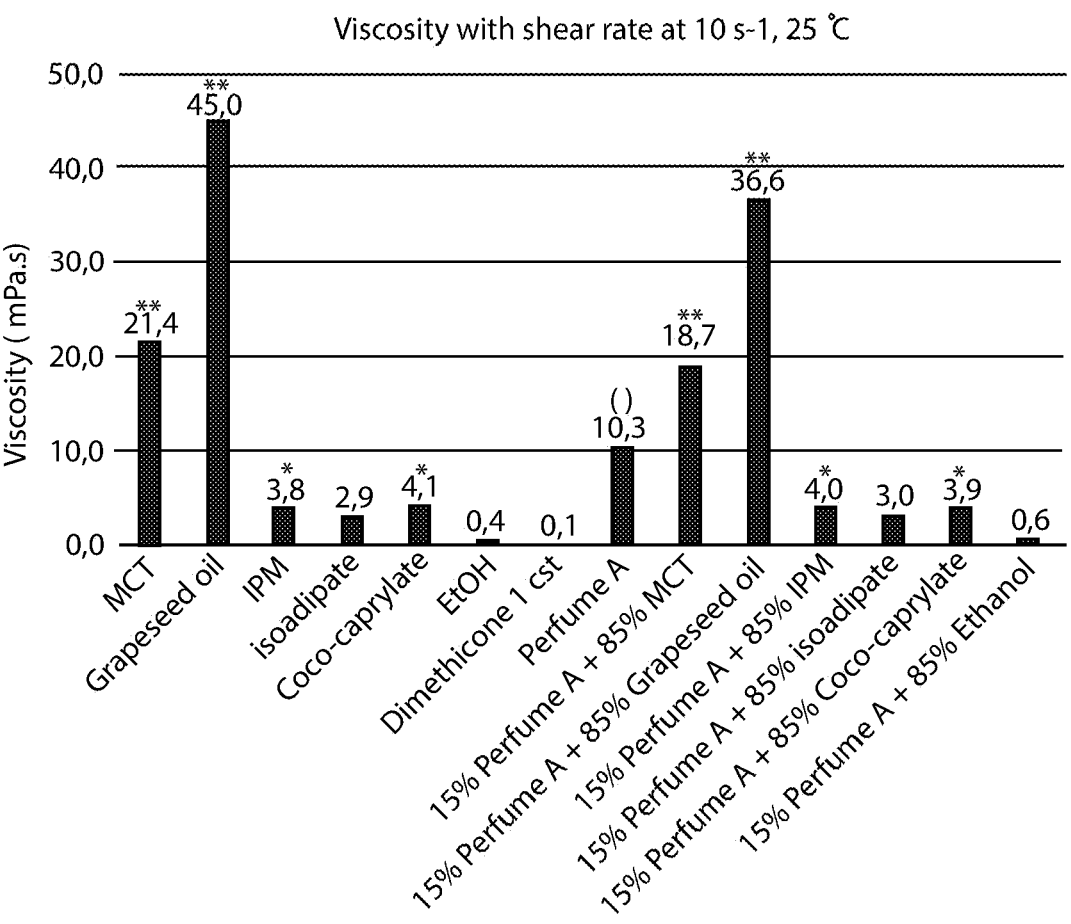
FIG. 3 describes the comparison of viscosities at 25° C. for a shear rate of 10 s$^{-1}$.

According to the invention, the capsule is seamless, of the core-shell type, and intended for fragrancing:

the shell comprising at least one hydrocolloid;

the core comprising at least one fragrancing agent and at least one lipophilic solvent;

characterized in that said shell is breakable, and in that the core comprises between 15 and 40% by weight of fragrancing agents relative to the total weight of the core and between 60 and 85% by weight of a non-glyceride lipophilic solvent relative to the total weight of the core, said solvent being miscible with ethanol and having:

a viscosity of less than 10 mPa·s as measured at a temperature of 25° C. and at a shear rate of 10 s$^{-1}$;
a specific gravity of between 0.82 and 0.99; and
a spreading value greater than 850 mm$^2$/10 min.

The invention has the advantage of providing a way to fragrance oneself on the go and in a new and unconventional manner. The user can, for example, extract a capsule at any time from a pillbox comprising a set of capsules according to the invention, and break it between his or her fingers. After breaking, the lipophilic core comprising the perfume composition is released and can advantageously be applied to the skin. The residual shell can be placed back in the pillbox or thrown directly into the trash. The capsule can be made entirely of food materials, natural or biosourced polymers, offering the advantage of being completely biodegradable or compostable.

An important technical advantage of the invention is that it allows encapsulation of a perfume composition using a judiciously chosen lipophilic (i.e. oily) solvent, which makes it possible to obtain, on the one hand, breakable and stable core-shell capsules, and, on the other hand, very good evaporation of the perfume and very good persistence. Indeed, it is known to those skilled in the art in the field of Perfumery, that in a conventional perfume composition, it is the presence of a large amount of ethanol which allows evaporation of the perfume by acting as a carrier for the perfume molecules and therefore enabling the fragrant effect. However, it is impossible to perform the encapsulation by co-extrusion, in particular, of a composition comprising a large amount of ethanol such as perfume compositions, because ethanol is hydrophilic and destabilizes the interface between the capsule core and its shell. Also, replacing ethanol with a conventional lipophilic solvent used in co-extrusion, such as glycerin vegetable oils or medium-chain triglycerides (MCT), will certainly make it possible to obtain core-shell capsules, but will prevent good evaporation of the perfume, since it is known that oils and other lipophilic solvents such as MCT greatly limit the diffusion of perfume molecules, these being retained ("weighted down") by the presence of lipophilic oil. Another notable disadvantage to the use of MCT, for example, is the persistent greasy feeling on the skin after application, and in addition the appearance of greasy stains on clothing.

Non-glyceride lipophilic solvents as defined according to the invention have the following advantages: good evaporation of the perfume composition, the absence of a persistent greasy feeling or of a greasy film during application to the skin, and the obtaining of a stable core-shell capsule. Furthermore, it is imperative that the solvents according to the invention be miscible with ethanol as well as with the perfume raw materials, and must not have any smell which would interfere with the odor of the perfume composition. "Miscible" is understood to mean that the solvent according to the invention can be mixed with perfume materials and with ethanol, forming a homogeneous mixture. Indeed, in addition to the perfume raw materials, the solvent according to the invention must be miscible with ethanol to address interface facilitation issues during the co-extrusion process enabling formation of the capsule. It may be necessary to use 0 to 10% ethanol to obtain a capsule, this ethanol evaporating during the drying of the capsules.

After application of a conventional perfume composition of 15% in ethanol, it is observed that evaporation reaches a level of at least 85% of the perfume composition at 70° C., and after 210 seconds. Evaporation is enabled due to the presence of ethanol which carries along the perfume molecules. Therefore, the more ethanol a perfume composition contains, the better the evaporation. Conversely, when a composition has a higher perfume concentration, such as 40% eau de parfum in ethanol, the proportion of ethanol is lower, which causes poorer evaporation of the perfume. This is one of the reasons why perfumes are never used pure, as they do not provide good evaporation. According to the invention, it is considered that "evaporation is good" when the perfume/lipophilic solvent mixture reaches an evaporation rate higher than 2% at 210 seconds, at 70° C. Even if this rate may seem low, it is in fact considered quite acceptable considering that lipophilic solvents as well as perfume molecules have extremely low evaporation rates (less than 2% at 210 seconds, at 70° C.).

The lipophilic solvents miscible in ethanol as defined according to the invention which make it possible to solve the technical problems raised are non-glyceride on the one hand, and on the other hand have:

a viscosity of less than 10 mPa·s as measured at a temperature of 25° C. and at a shear rate of 10 s⁻¹;
  a specific gravity of between 0.82 and 0.99; and
  a spreading value greater than 850 mm²/10 min.

A solvent meeting the above parameters advantageously makes it possible to implement the capsule according to the invention. The viscosity and spreading values as defined above allow optimum spreading of the lipophilic perfume composition on the skin, with virtually no appearance of a film or greasy feeling, while ensuring good evaporation of the perfume. The range of specific gravity values allows the co-extrusion process to be carried out in an optimal manner.

The capsule core comprises a main quantity of a non-glyceride lipophilic solvent. Indeed, the use of a glyceride type of solvent leads to the formation of a persistent greasy film on the skin which can be unpleasant for the user, which is undesirable. Advantageously, said core contains less than 5% by weight of a glyceride solvent. Even more preferably, the core is essentially devoid of glyceride solvent.

Preferably, the non-glyceride lipophilic solvent represents between 70 and 80% by weight relative to the weight of the capsule core.

The non-glyceride solvents according to the invention are selected among esters, silicones, and vegetable and mineral oils. Preferably, vegetable oils will be used in order to obtain the most biosourced capsule possible and therefore preferably biodegradable.

Preferably, the lipophilic solvent is selected among isoadipate, coco-caprylate, isopropyl myristate, and dimethicone 1 cSt.

The specific gravity of the non-glyceride lipophilic solvent is between 0.82 and 0.89. By definition, the specific gravity at 20° C. corresponds to the ratio of the density of said composition or solvent at 20° C. to the density of water at 4° C.

The choice of this specific gravity range ensures good co-extrusion during the manufacture of capsules by a process referred to as co-extrusion. Advantageously, the specific gravity of the total composition of the core (i.e. of ethanol, of fragrancing agent(s), and of lipophilic solvent(s)) is between 0.82 and 0.99.

The non-glyceride solvent according to the invention must have a spreading value greater than 850 mm²/10 min. The spreading value of a substance is defined as the ability of said substance to cover a surface in 10 min. This parameter makes it possible to characterize a perfume/lipophilic solvent composition so that it is as non-oily as possible and leaves the least trace of oil on the skin after application. Advantageously, the spreading value of a lipophilic solvent (selected among esters, silicones, and vegetable and mineral oils) can be calculated using equations given in the literature such as in the publication by M. Douguet et al. (Spreading properties of cosmetic emollients: Use of synthetic skin surface to elucidate structural effects—Colloids and Surfaces B: Biointerfaces 154 (2017) 307-314). Indeed, after statistical analyses by partial least squares regression, it was found that the viscosity measured at 25° C. (x) is the most reliable variable for predicting the spreading value (y) as a function of the nature of the lipophilic solvent, according to a logarithmic regression as described below:

for esters (IPM, isoadipate, and coco-caprylate in our study):

$$y = -225 \times \log(x) + 1315; \qquad \text{[Math. 1]}$$

for silicones (octamethyltrisiloxane and polydimethylsiloxane dimethicones in our study):

$$y = -222 \times \log(x) + 1670; \qquad \text{[Math. 2]}$$

for vegetable oils (MCT and grapeseed oil in our study):

$$y = -101 \times \log(x) + 748; \qquad \text{[Math. 3]}$$

for mineral oils:

$$y = -140 \times \log(x) + 975. \qquad \text{[Math. 4]}$$

When the capsule core comprises several fragrancing agents, the total quantity of the mixture of fragrancing agents is between 15 and 40% by weight relative to the total weight of the capsule core.

The fragrancing agents that can be encapsulated in the capsule according to the invention can be natural products such as extracts, "jungle essence" extracts, essential oils, absolutes, resinoids, resins, concretes, etc., but also synthetic products (also called captive odorants) such as hydrocarbons, alcohols, aldehydes, ketones, ethers, acids, esters, acetals, nitriles, etc., in particular saturated or unsaturated, aliphatic, heterocyclic, or carbocyclic compounds. Such odorant substances are mentioned, for example, in S. Arctander, "Perfume and Flavor Chemicals" (Montclair, N.J., 1969), or in "Common Fragrance and Flavor Materials", Wiley-VCH, Weinheim, 2006.

In addition to fragrancing agents and the non-glyceride solvent, the capsule core can advantageously comprise fixing agents. "Fixing agent" is understood to mean an ingredient, perfumed or not, which allows prolonging the retention of a perfume on the skin. More specifically, a fixing agent is a compound that can equalize the vapor pressures (therefore the volatilities) of the raw materials in a perfume oil, to increase its tenacity. The fixing agents which can be encapsulated with the fragrancing agents and solvent according to the invention can be selected from the following non-exhaustive list: absolutes, concretes, resins and oleoresins, waxes, derivatives of glucose, of sucrose, of sorbitol, of citric acid and salicylic acid, celluloses (in particular ethylcellulose), seaweed extracts, triglycerides, oils such as castor oil and its derivatives, emollients such as certain esters for example ethylhexylglycerin, polymers and their mixtures, polyurethanes, polyamides, certain silicones, liquid paraffin, glycol, fumed silica, and quaternary ammonium salts.

In the invention, the term "capsule" designates a system of membrane encapsulation of a composition, said capsule having a core-shell structure, the encapsulated composition comprising "the core" which is enclosed in a shell (or core-shell) consisting of a coating material.

The capsule according to the invention differs from a matrix system where the composition is dispersed in a continuous matrix of a material and which is generally designated by the term "microsphere".

The fact that the capsule is seamless makes it possible to avoid the presence of a breaking point located at the seal between two half-shells forming the capsule, as is the case with "softgel" capsules. The seamless capsule thus offers the advantage of avoiding leaks related to a rupture of the seam.

The term "breakable capsule" refers to a capsule as defined above, in which the shell can be broken by means of pressure applied to the outer surface of the capsule when the capsule is grasped between the fingers or pressed against the skin to release the core contained in the shell.

The capsule according to the invention preferably has a hardness of between 0.5 and 2.5 kg. The breaking resistance (or hardness) is measured by the crushing force to be exerted in order to break the capsule and by the deformation (and therefore the elasticity) of the capsule when pressure is applied. More preferably, the capsule has a hardness of between 0.8 and 2 kg. The hardness of the capsules is measured by a TA.XT Plus texture analyzer on 20 capsules with a P0.5 piston at a speed of 0.50 mm/s; the hardness is expressed in kg and the elasticity as the deformation percentage (%) at break.

According to a preferred embodiment of the invention, the core of the breakable capsule according to the invention represents 50 to 95% by weight of said capsule, preferably 80 to 92%, more preferably 85 to 92%.

Advantageously, the thickness of the capsule core-shell is 10 to 500 microns, preferably 30 to 150 microns, more preferably 50 to 80 microns; the outer diameter of the capsule is between 2 and 10 mm, preferably 3 to 5 mm, more preferably 3.4 to 4.8 mm, and even more preferably 3.5 to 4.5 mm; the ratio of capsule diameter to shell thickness is within the range of 10 to 100, preferably 50 to 70.

The capsule core-shell according to the invention advantageously comprises at least one hydrocolloid. Preferably, the hydrocolloid according to the invention is a biobased polymer. Biobased polymer is understood to mean a synthetic polymer partially (generally >20%) or entirely obtained from biomass derivatives. The biobased nature of a polymer can be determined in particular from its C14 content, according to the ASTM D6866 standard.

The hydrocolloid constituting the core-shell of the capsule is selected among gellan gum, gelatin (of animal origin or biotechnological origin), collagen, alginates, carrageenans, agar-agar, chitosan and its derivatives, pectins, gum arabic, ghatti gum, pullulan gum, mannan gum, starches and starch derivatives, plant proteins, or modified cellulose, used alone or as a mixture. The quantity of said hydrocolloid(s) present in the core-shell is from 1.5 to 95% by weight, preferably from 4% to 75% by weight, and even more preferably from 20% to 50% by weight relative to the total dry weight of the core-shell envelope. In a preferred embodiment, the selected hydrocolloid is gellan gum used alone or in combination with gelatin. In another preferred embodiment, the hydrocolloid is selected from the carrageenans.

According to one embodiment, the dry weight of the core-shell is between 8-50%, preferably 8-20%, more preferably 8-15%, by weight relative to the total dry weight of the capsule.

In another embodiment of the invention, the capsule comprises a moisture barrier coating. In this embodiment, the capsule core-shell is coated with at least one moisture barrier layer comprising at least one moisture barrier agent dispersed in an organic solvent or in an aqueous solution or suspension. In this embodiment, the shell may consist of any hydrocolloid used alone or in a mixture, with or without gelatin. The gelatin can also constitute the only gelling agent of the shell. However, preferably, even in the presence of the hydrophobic coating, the shell also comprises an amount of gellan gum, or agar, or carrageenans or alginates, or gum arabic, or pectins, or pullulan gum, or mannan gum, sufficient to provide some resistance to humidity; in this case, the shell may comprise from 1.5 to 95% by weight, preferably 4% to 75% by weight, and even more preferably from 20% to 50% by weight, relative to the total dry weight of the shell of at least one hydrocolloid selected from the group consisting of gellan gum, agar, carrageenans, and pullulan gum. According to another embodiment of the invention, the core-shell of the coated capsule comprises gellan gum, or arabic gum, or pectins, or agar, or alginates, or carrageenans, or ghatti gum, or pullulan gum, or mannan gum, or a mixture thereof, but does not comprise gelatin.

Advantageously, the capsule core-shell may be covered with at least one moisture barrier agent which is at least one hydrophobic agent selected among those suitable for pharmaceutical or cosmetic products, preferably selected from the group consisting of waxes, in particular carnauba wax, candelilla wax or beeswax, poultry wax, shellac (in alcoholic or aqueous solution), ethyl cellulose, hydroxypropyl methylcellulose, hydroxypropyl cellulose, latex composition, polyvinyl alcohol, or a combination thereof. More preferably, the at least one moisture barrier agent is ethyl cellulose or a mixture of ethyl cellulose and shellac. According to another embodiment of the invention, the hydrophobic moisture barrier agent can be a combination of hydroxypropyl methylcellulose, plasticizer, cellulose, and microcrystalline color. According to another embodiment of the invention, the hydrophobic moisture barrier agent is a film-forming gelling agent, preferably gellan gum itself.

The core-shell may further comprise at least one plasticizer, which may be glycerol, sorbitol, maltitol, triacetin, or polyethylene glycol, or another polyalcohol with plasticizing properties, and possibly an acid of the monoacid, diacid, or triacid type, in particular citric acid, fumaric acid, malic acid, and the like. The amount of plasticizer ranges from 1% to 30% by weight, preferably from 2% to 15% by weight, and even more preferably from 3 to 10% by weight, of the total dry weight of the core-shell.

The core-shell may advantageously comprise a coloring agent which can make more attractive the capsule comprising the perfumed composition. The coloring agent is preferably selected from dyes and pigments of food or cosmetic origin. The coloring may be in the body of the core-shell or applied by an additional coating process.

Bulking agents can also be included in the composition of the core-shell; bulking agent is understood to mean any suitable material that can increase the percentage of dry matter in the external liquid phase and therefore after co-extrusion in the capsule shell obtained. The increase in the quantity of dry matter in the capsule shell has the result of solidifying said shell and making it physically more resistant. Preferably, the bulking agent is selected from the group comprising starch derivatives such as dextrin, maltodextrin, cyclodextrin (alpha, beta, or gamma), or cellulose derivatives such as hydroxypropyl methylcellulose (HPMC), hydroxypropyl cellulose (HPC), methyl cellulose (MC), carboxymethyl cellulose (CMC), polyvinyl alcohol, polyols, or mixtures thereof. Dextrin is the preferred bulking agent. The amount of bulking agent in the core-shell is at most 98.5%, preferably 25 to 95%, more preferably 40 to 80%, and even more preferably 50 to 60%, by weight of the total dry weight of the core-shell.

Advantageously, when the capsule according to the invention is broken and the perfumed composition applied to the skin, it does not leave a greasy feeling on the skin.

The second object of the invention relates to a method for manufacturing a breakable capsule comprising a shell and a core, for fragrancing a user, comprising the steps of:

(A) co-extrusion of a hydrophilic external liquid phase and a lipophilic internal liquid phase, the external liquid phase comprising from 4 to 95% by weight of a hydrocolloid relative to the dry weight of said external phase;

the internal liquid phase comprising from 15 to 40% by weight of fragrancing agents relative to the total weight of the core, from 0 to 10% by weight of ethanol relative to the total weight of the core, and from 60 to 85% by weight of a non-glyceride lipophilic solvent relative to the total weight of the core, said solvent being miscible with ethanol and having:

a viscosity of less than 10 mPa·s as measured at a temperature of 25° C. and at a shear rate of 10 s$^{-1}$;

a specific gravity of between 0.82 and 0.99; and a spreading value greater than 850 mm$^2$/10 min;

(B) solidification and/or gelation of the surface of the capsules thus obtained, by immersion in a cold bath at a temperature of between 1° C. and 20° C.;

(C) washing and drying the capsules; and (D) collecting the capsules.

The co-extrusion process is a synchronous extrusion of two liquids: the hydrophilic external liquid phase, and the lipophilic internal liquid phase. The co-extrusion process consists of three main steps: drop formation, solidification of the shell, and collection of the capsules. The capsules of the invention can be produced by any suitable co-extrusion process. Preferably the capsules are produced by a device and method as described in EP 513603.

According to one embodiment of the invention, after the co-extrusion step, the solidification step is carried out while keeping the capsules cold in order to ensure good gelation of the shell, for example by placing them in contact with a cold bath. The cold bath is preferably cold oil. Cold within the meaning of the invention is understood to mean a temperature of between 1 and 20° C., preferably 2 and 10° C., more preferably between 4 and 6° C. The capsules can then be centrifuged to remove the excess oil, possibly washed with an organic solvent—also to remove excess oil—and dried. According to one embodiment of the invention, after co-extrusion step, and optionally the solidification step, the capsules are centrifuged.

According to another embodiment of the invention, the capsules are co-extruded, centrifuged, and possibly immersed in a solution or an emulsion containing an agent which allows hardening the shell of the capsules, or a hardening agent.

The hardening agent can also be ethanol or any other anhydrous organic solvent, maintained at a temperature of between 0 and 25° C., more particularly between 10 and 20° C.

The hardening agent can also be a calcium ion bath, for example of calcium chloride, dicalcium phosphate, or calcium sulfate, or an acid bath containing calcium ions with a pH of less than 5, preferably from 3 to 4. Example acids can be adipic acid, fumaric acid, gluconic acid, or glucono-delta-lactone. The calcium ion or acid bath is preferably at a temperature of 0 to 25° C., preferably 10 to 20° C.

The immersion step has the effect of washing away the remaining oil at the periphery of the capsule, and gradually reinforcing the core-shell, in particular by dehydration and osmotic balance.

According to one embodiment of the invention, after immersion, the capsules are dried in a stream or in air at controlled temperature and humidity. The relative humidity of the drying air is 20% to 60%, preferably 30 to 50%; the drying air temperature is 15 to 60° C., preferably 35 to 45° C. If necessary, the surface oil can be eliminated using an adsorbent such as starch added during drying, between 0.1 and 5%, preferably between 0.1 and 2%.

According to another embodiment, the method according to the invention further comprises a coating step during which the outer moisture barrier layer is applied to the capsules. Preferably, said coating step is carried out by immersing the capsules in a coating solution, or by spraying a coating solution on the capsules. Said coating step is preferably carried out after the drying step.

Capsules made by the method of the invention are essentially or perfectly spherical and are very uniform in size.

A third object of the application relates to the use of a capsule according to the invention, to fragrance a user. Once the capsule is broken, the perfume composition does not leave a greasy feeling on the skin after application to the skin.

A fourth and final object of the application relates to a method for fragrancing a user, characterized in that it comprises the following steps:

gripping the capsule according to the invention between two of the user's fingers;

rupturing said capsule by the action of a pressure enabling said capsule to be broken between the two fingers;

applying the oily perfumed composition contained in the capsule to the skin.

The invention is illustrated below by the following examples, which are not be considered as limiting the scope of the invention, and are to be read with reference to the figures.

EXAMPLES

Several oils are studied. Their miscibility with perfume, their compatibility with the co-extrusion process, and their greasy appearance are compared. They are listed below:

MCT: medium-chain triglyceride oil of the C8-C10 type (with a molecular weight equal to 387.5 g/mol);

IPM: Isopropyl myristate, synthetic oil (ester of myristic acid and isopropanol);

Coco-caprylate: emollient of natural origin;

Isoadipate: diester of isopropyl alcohol and adipic acid produced by synthesis;

Grapeseed oil: natural oil;

Octamethyltrisiloxane: dimethicone with a molecular weight of 236.53 g/mol, whose viscosity is 1 cSt (or $10^{-6}$ m$^2$/s);

Polydimethylsiloxane (polymer): dimethicone with a viscosity of 10 cSt (or $10^{-5}$ m$^2$/s).

For this study, the physicochemical properties of these oils are compared to those of ethanol, a solvent used in fine perfumery.

Four different perfumes are tested, hereinafter called Perfume A, Perfume B, Perfume C, and Perfume D. These perfumes are composed for application in fine perfumery.

In order to study the impact of various oils on the evaporation of each perfume, two different perfume concentrations are produced, respectively to mimic the composition of eau de toilette and of perfume (i.e. respectively 15% and 40% of perfume in the oil). In addition, these two compositions comprise 5% ethanol (see Table 2). Each final mixture must be homogeneous and have a specific gravity which must be between 0.82 and 0.99.

Specific Gravity

The specific gravity of the various perfume/oil/ethanol mixtures is measured (Table 2) using an Anton Paar hydrometer with temperature control in order to find out whether the various oils can be used in the co-extrusion operation.

TABLE 1

|  | Composition | |
| --- | --- | --- |
|  | 15% perfume | 40% perfume |
| Perfume | 15% | 40% |
| Oil | 80% | 55% |
| Ethanol | 5% | 5% |

Mass percent composition of the mixtures used for the specific gravity measurement

TABLE 2

|  | 15% perfume | 40% perfume |
| --- | --- | --- |
| IPM | 0.863 | 0.89 |
| MCT | 0.938 | 0.943 |

TABLE 2-continued

|  | 15% perfume | 40% perfume |
| --- | --- | --- |
| Isoadipate | 0.952 | 0.95 |
| Coco-caprylate | 0.893 | 0.91 |
| Grapeseed oil | 0.919 | 0.928 |
| Octamethyltrisiloxane | 0.842 | 0.875 |
| Polydimethylsiloxane | 2 phases | 2 phases |

Specific gravities measured at room temperature for the mixtures used in co-extrusion at 15% and 40% perfume The results show that a 10 cSt dimethicone (a polydimethylsiloxane) as a lipophilic solvent does not allow achieving a homogeneous mixture with the perfume and ethanol, because we end up with two phases. On the other hand, all the other mixtures are homogeneous and therefore the other lipophilic solvents studied are suitable for the co-extrusion operation.

Viscosity

The rheological behavior is studied with a Haake MARS III rheometer. The measurements are taken at 25° C. with a 5 mm cone with an angle of 2 degrees, during rotation, in order to express the viscosity (q) expressed in mPa·s as a function of the shear rate expressed in s$^{-1}$, for the purpose of measuring the viscosity of the different oils alone (FIG. 1) or mixed with the perfume in a perfume/oil mass ratio of 15/85 (FIG. 2). The values considered are those for a shear rate of 10 s$^{-1}$.

A study at 70° C. was also carried out on several oils in order to verify the differences observed (Table 3). The viscosity decreases significantly. Ascending order is maintained, however.

TABLE 3

| Ref | Viscosity at 25° C. (mPa · s) 10 s$^{-1}$ | Viscosity at 70° C. (mPa · s) 10 s$^{-1}$ |
| --- | --- | --- |
| Isoadipate | 2.9 | 0.7 |
| IPM | 3.8 | 1.6 |
| Coco-caprylate | 4.1 | 1.5 |
| MCT | 21.4 | 4.9 |
| Grapeseed oil | 45.0 | 10.8 |

Comparison of viscosity values (for shear rate at 10 s$^{-1}$) measured at 25° C. and 70° C.

FIG. 3 shows the viscosity values at 25° C. at a shear rate of 10 s$^{-1}$, with assessments of greasiness on the skin (perfume alone was not tested for toxicological reasons). There is a clear difference between the viscosity of MCT and of grapeseed oil, 21.4 and 45.0 mPa·s respectively, compared to that of other oils or of ethanol. The threshold of 10 mPa·s separates oils that are too greasy from those appreciated for their pleasant or even dry finish. In conclusion, MCT as well as grapeseed oil are not suitable.

Spreading

The spreading data are calculated (see FIG. 4) using logarithmic regression formulas given in the literature, such as in the publication by M. Douguet et al. (Spreading properties of cosmetic emollients: Use of synthetic skin surface to elucidate structural effects—Colloids and Surfaces B: Biointerfaces 154 (2017) 307-314). In this publication, 53 emollients (among esters, silicones, and vegetable and mineral oils) were characterized and the impact of three physicochemical parameters (viscosity, surface tension, and specific gravity) on the spreading value was studied. After statistical analyses by partial least squares regression, it was found that the viscosity measured at 25° C. (x) is the most reliable variable for predicting spreading (y) as a function of the nature of the emollient, according to a logarithmic regression as described below:

for esters (IPM, isoadipate, and coco-caprylate in our study):

$$y = -225 \times \log(x) + 1315; \qquad \text{[Math. 5]}$$

for silicones (octamethyltrisiloxane and polydimethylsiloxane dimethicones in our study):

$$y = -222 \times \log(x) + 1670; \qquad \text{[Math. 6]}$$

for vegetable oils (MCT and grapeseed oil in our study):

$$y = -101 \times \log(x) + 748. \qquad \text{[Math. 7]}$$

Using the viscosity values as measured and summarized in Table 3 above, the spreading values are calculated using the above equations (Table 4). The vegetable oils in our study have a spreading value classified as "medium" (from 500 to 850 mm$^2$/10 min), whereas the favored oils according to the invention have a spreading value classified as "high" (greater than 850 mm$^2$/10 min).

Evaporation

Evaporation of the perfume in a mixture with ethanol or with an oil is analyzed by following the evolution of a sample's mass during heat treatment. This study is carried out using a Mettler Toledo—HX204 Halogen Moisture Analyzer balance.

fumes A, B, C, and D. Consequently, subsequent analyses by heat treatment will be carried out below for only 30 min (and not 2 hours).

Pure Oil or Pure Perfume

Figures 6, 7:
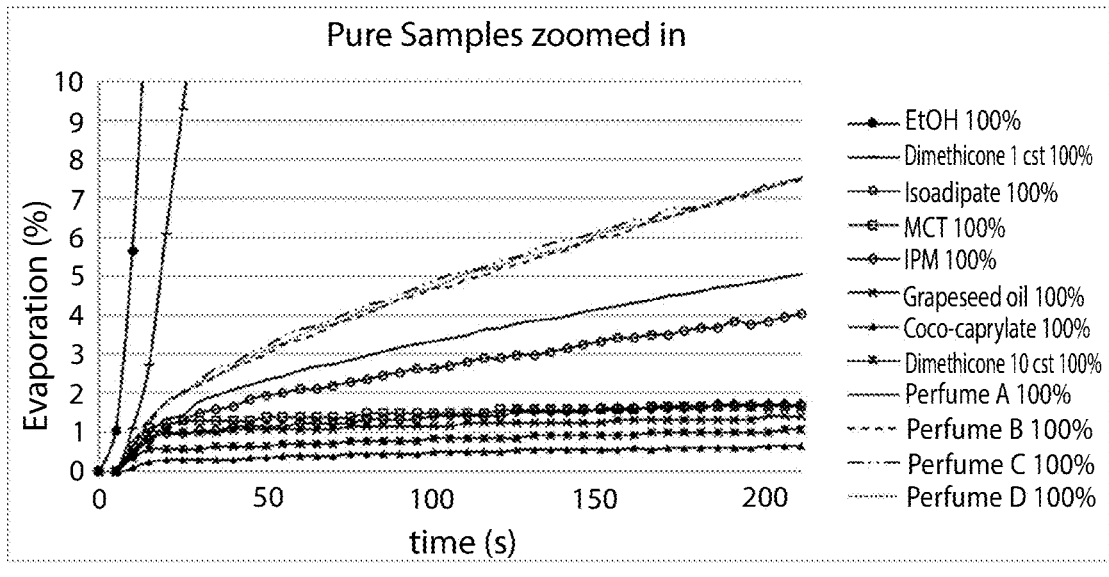
FIG. 6 describes the evaporation profile of pure oils and pure perfumes.
FIG. 7 describes the evaporation profile of pure oils and pure perfumes, zoomed in on the small values.

At 210 seconds, all oils have a much lower evaporation capacity than ethanol (100%), equal to 1.7%, 1.7%, 4.0%, 0.7%, and 1.4% respectively for MCT, IPM, isoadipate, coco-caprylate, and grapeseed oil. An exception is dimethicone 1 cSt which has an evaporation capacity of 82.5%. This evaporation capacity is also lower than that of the pure perfumes which have an evaporation capacity of 5.1%, 7.5%, 7.5%, and 7.5% respectively for perfume A, perfume B, perfume C, and perfume D (see FIG. 6 and FIG. 7).

Perfume/Ethanol Mixture vs Perfume/Oil Mixture According to the Invention

Figure 8:
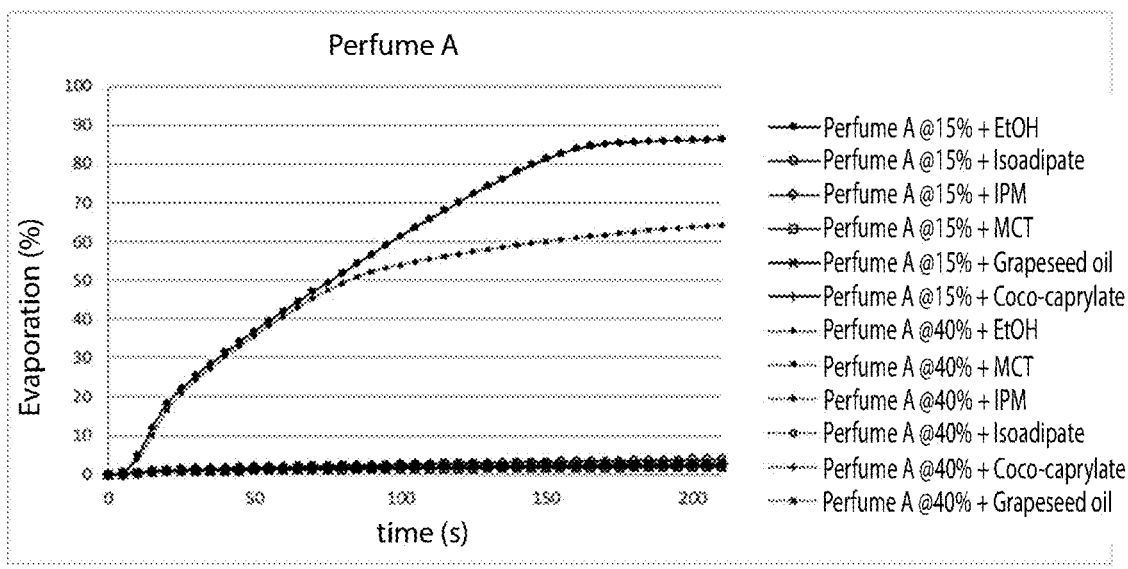
FIG. 8 describes the evaporation profile of perfume A at 15% and 40% in different oils, compared to that with ethanol.
Figure 9:
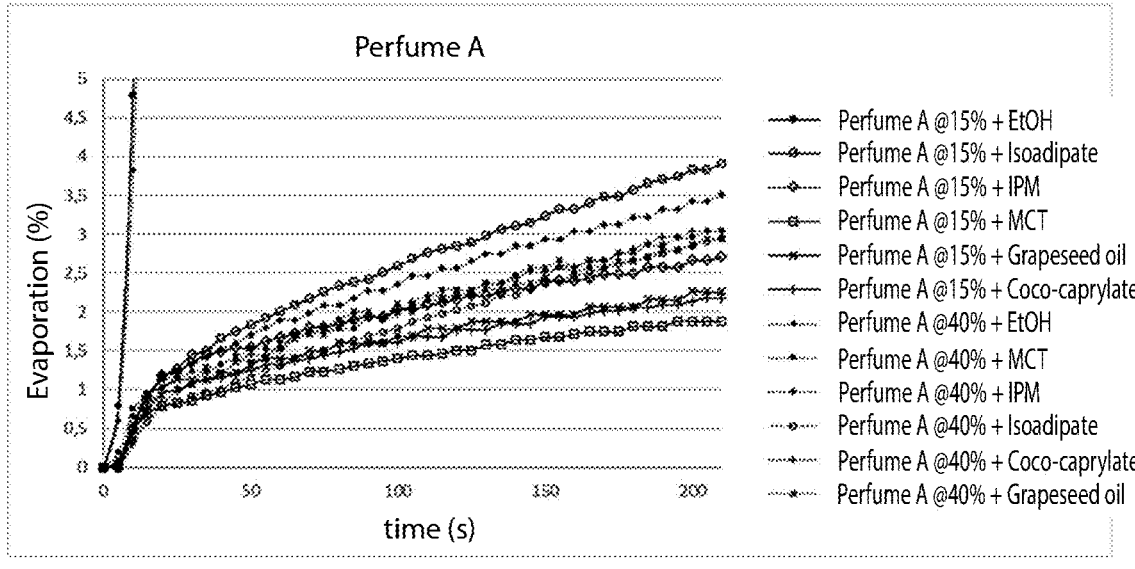
FIG. 9 describes the evaporation profile of perfume A at 15% or 40% in different oils, compared to that with ethanol with a zoom-in on small values.
Figure 10:
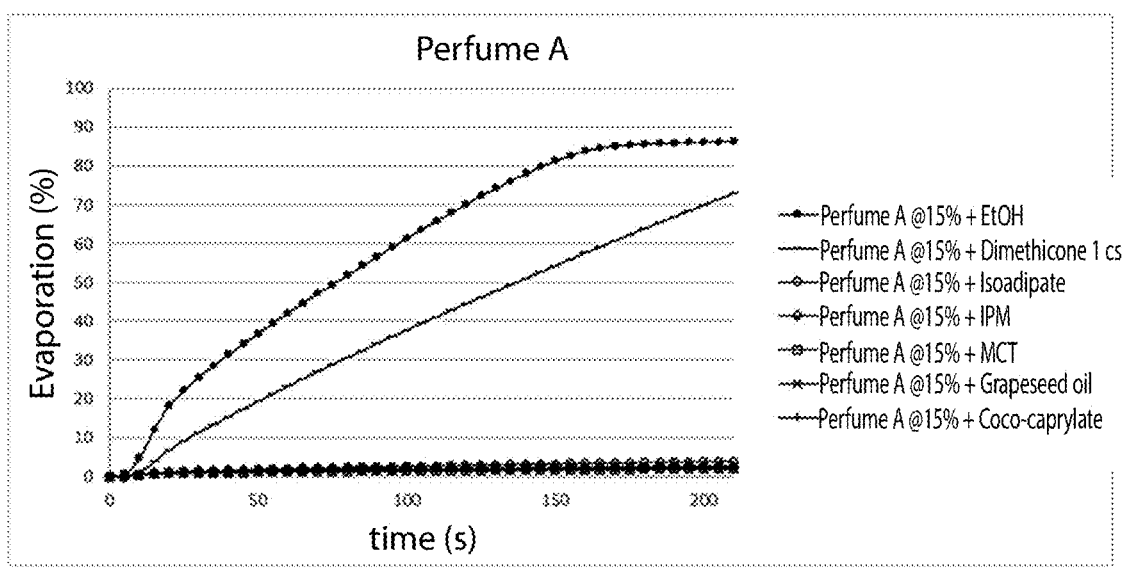
FIG. 10 describes the evaporation profile of perfume A at 15% in different oils, compared to that with ethanol.
Figure 11:
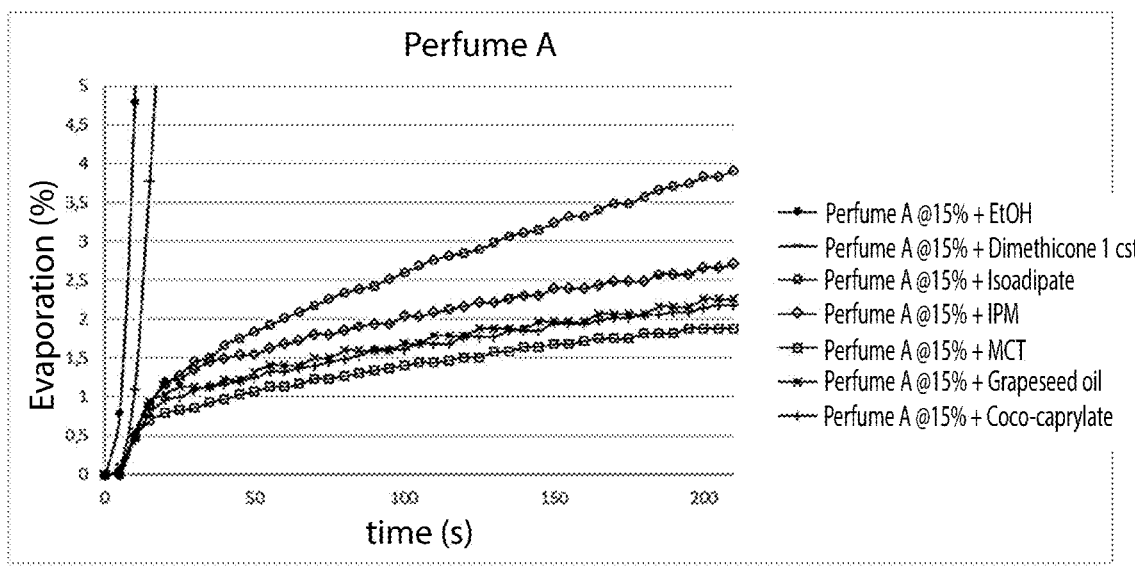
FIG. 11 describes the evaporation profile of perfume A at 15% in different oils, compared to that with ethanol, zoomed in on the small values.
Figure 12:
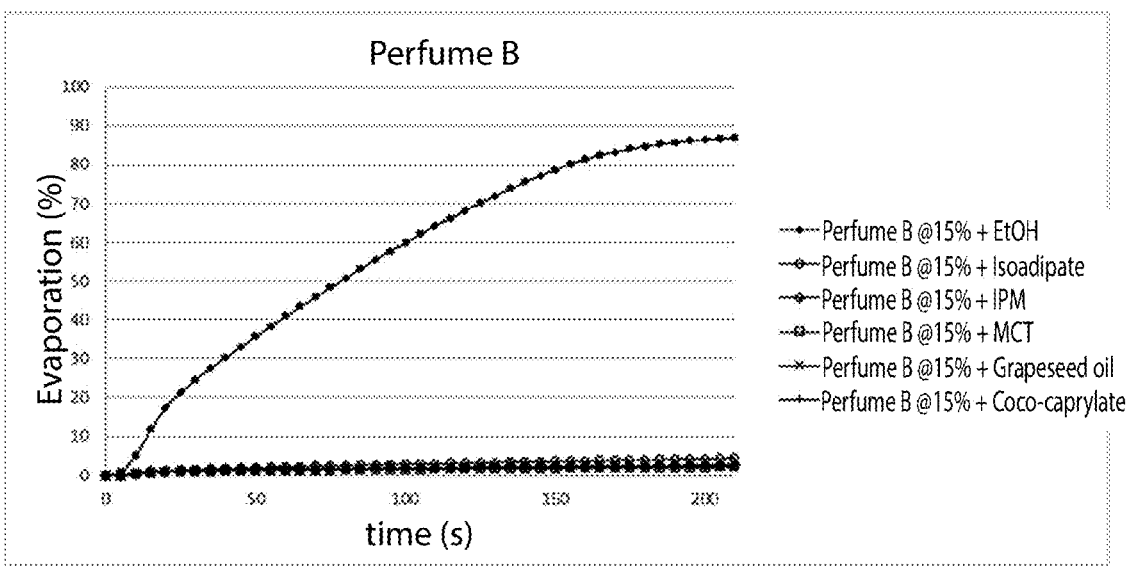
FIG. 12 describes the evaporation profile of perfume B at 15% in different oils, compared to that with ethanol.
Figure 13:
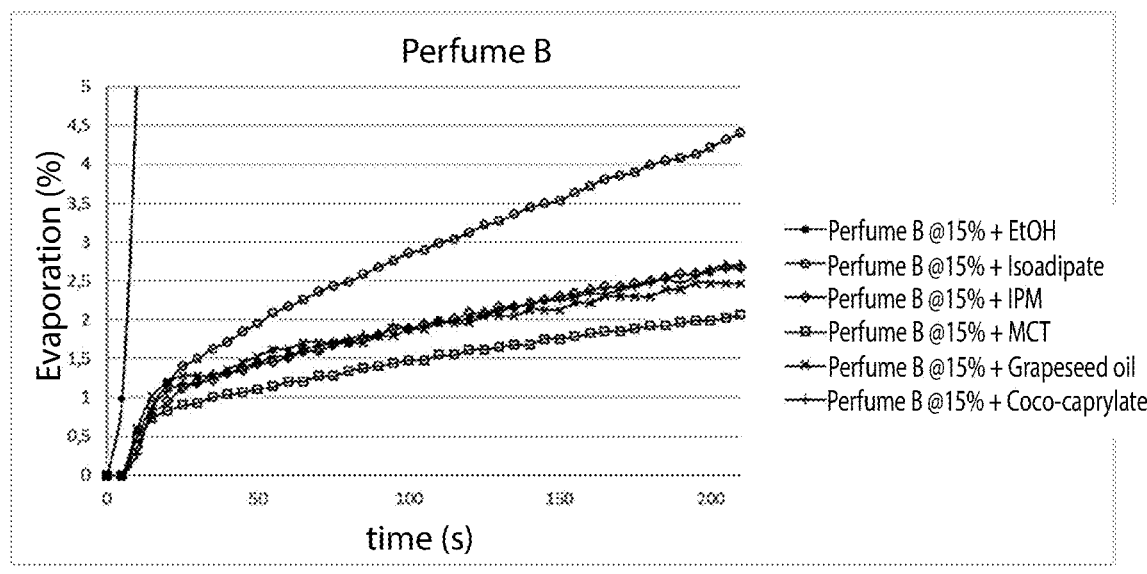
FIG. 13 describes the evaporation profile of perfume B at 15% in different oils, compared to that with ethanol, zoomed in on the small values.
Figure 14:
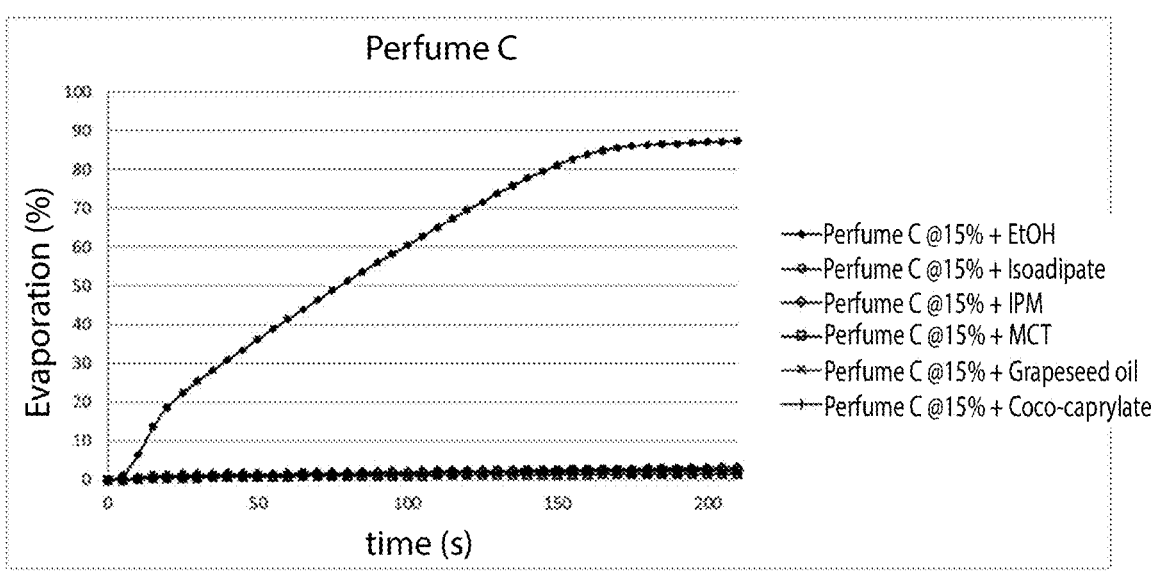
FIG. 14 describes the evaporation profile of perfume C at 15% in different oils, compared to that with ethanol.
Figure 15:
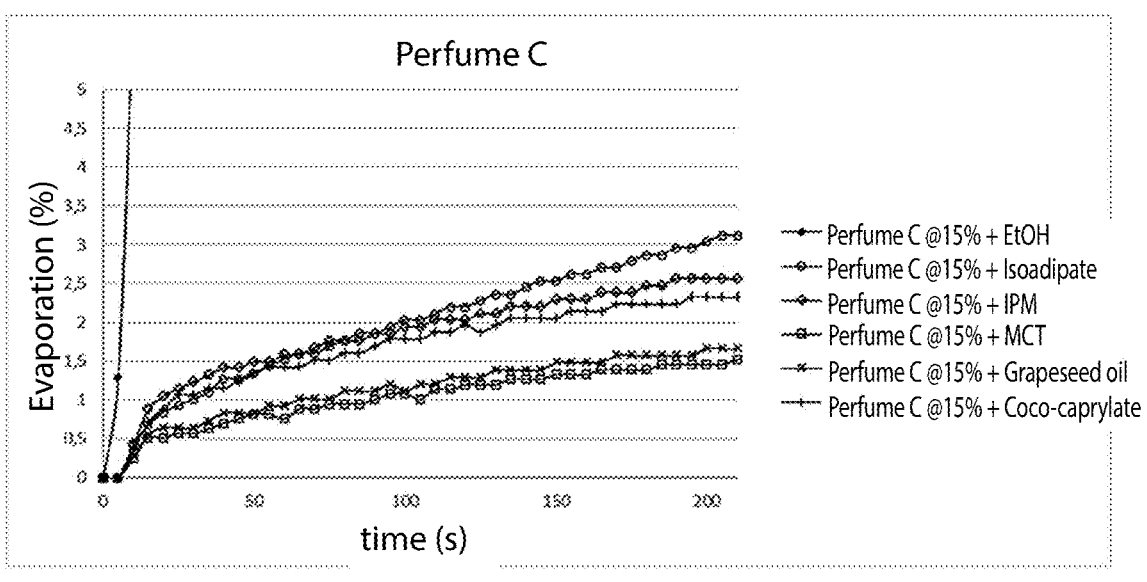
FIG. 15 describes the evaporation profile of perfume C at 15% in different oils, compared to that with ethanol, zoomed in on the small values.
Figure 16:
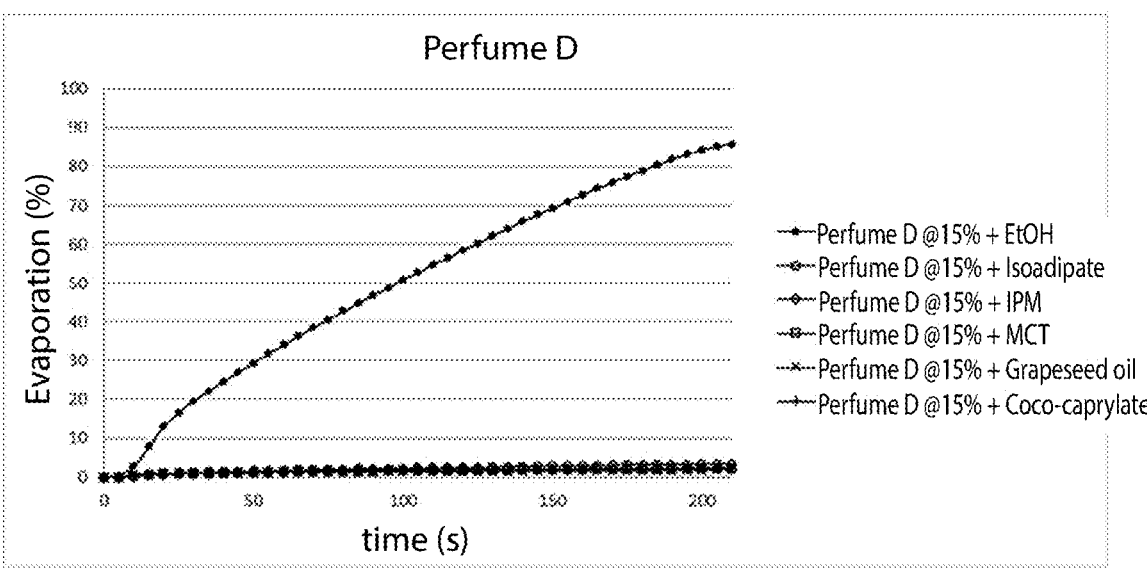
FIG. 16 describes the evaporation profile of perfume D at 15% in different oils, compared to that with ethanol.
Figure 17:
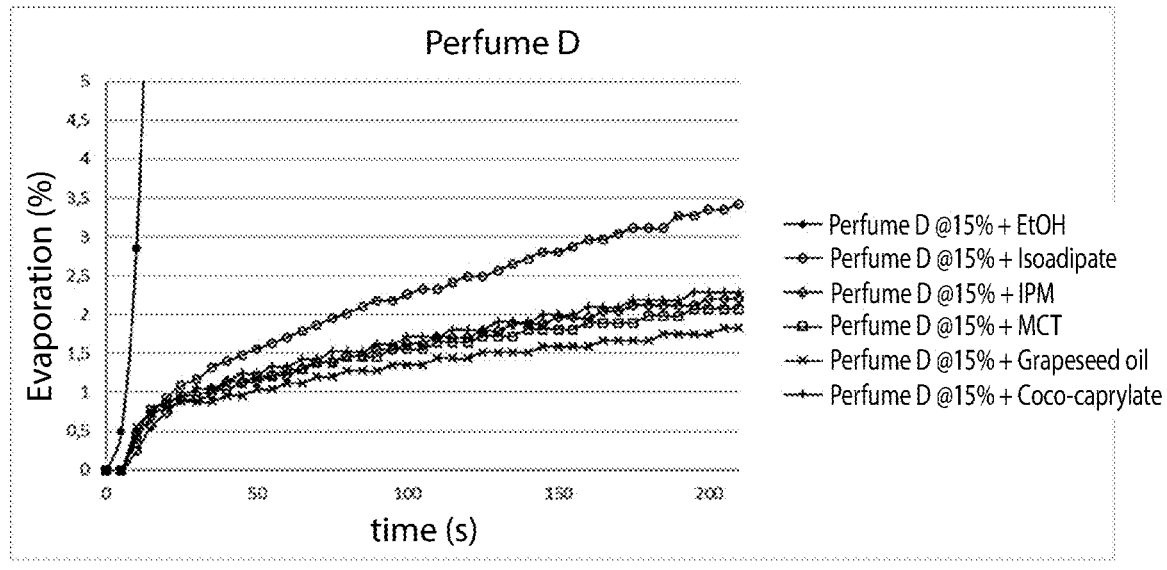
FIG. 17 describes the evaporation profile of perfume D at 15% in different oils, compared to that with ethanol, zoomed in on the small values.

Samples with a 40% concentration of perfume A by weight were created with different oils. Since perfume has a higher evaporation capacity than oils, the analyses confirm that the higher the perfume concentration, the better the evaporation (see FIG. 8 and FIG. 9).

For samples with a 40% concentration of perfume by weight, results of the analyses at 210 seconds show that MCT does not allow evaporation greater than 2% for any of perfumes A, B, C, or D. Grapeseed oil does not allow evaporation greater than 2% for perfumes C or D. On the other hand, the other oils all allow evaporation greater than 2% regardless of the perfume (see FIGS. 10 to 17).

CONCLUSION

The physicochemical characterization of oils of different natures (esters, vegetable oils, and silicones) makes it possible to study their compatibility with the extrusion operation in a mixture with a fine perfumery perfume, and with the expected sensory finish, in comparison with a conventional alcohol-based mixture of a fine perfumery perfume. Table 4 below summarizes the data.

TABLE 4

|  | Vegetable oils | | Esters | | | Silicones | | |
|---|---|---|---|---|---|---|---|---|
|  | MCT | Grape seed oil | IPM | Isoadipate | Coco-caprylate | octamethyl trisiloxane | polydimethyl | EtOH |
| CAS number | 73398-61-5 | N/A | 110-27-0 | 6938-94-9 | 107525-85-9 | 107-51-7 | N/A | 64-17-5 |
| Molecular weight (g/mol) | 387.52 | 279.51 | 270.5 | 230.3 | 280 | 236.53 | N/A | 46.07 |
| Density | 0.930-0.960 | 0.920-0.926 | 0.85-0.855 | 0.960-0.970 | 0.856-0.862 | 0.816 | 0.934 | 0.789 |
| Miscibility of perfume/oil/EtOH mixture | yes | yes | yes | yes | yes | yes | no | N/A |
| Viscosity (mPa · s) 10 s$^{-1}$, 25° C. | 21.4 | 45.0 | 3.8 | 2.9 | 4.1 | 0.1 | 8.2 | 0.4 |
| Viscosity (mPa · s) 10 s$^{-1}$, 70° C. | 4.9 | 10.8 | 1.6 | 0.7 | 1.5 |  |  |  |
| Greasy appearance | +++ | +++ | + | 0 | + | 0 | 0 | 0 |
| Calculated spreading (mm$^2$) | 614 | 581 | 1185 | 1211 | 1177 | 1959 | 1467 | N/A |
| Evaporation at 210 s of mixture with 15% perfume | <2% | <2% | >2% | >2% | >2% | >2% | >2% | >85% |

Comparison of physicochemical data of the oils studied 1 g of sample is deposited drop by drop on a paper filter in an aluminum dish. The analysis is carried out at 70° C.

The first analyses are carried out for 2 hours, the goal being to determine the evaporation "plateau" region, i.e. the time required to reach maximum evaporation.

Standard Perfume/Ethanol Mixture

The test results show that at least 85% of the evaporation of standard perfume/ethanol mixtures (in a mass ratio of 15/85) is obtained after 210 seconds or 3.5 minutes (see FIG. 5): 86.5%, 87.6%, 87.2%, and 85.8% respectively for per- The oil/perfume/ethanol mixtures all have a specific gravity enabling co-extrusion, but the mixtures made with polydimethylsiloxane (dimethicone 10 cSt) are not homogeneous. This dimethicone 10 cSt is therefore not indicated as a solvent for the invention, since it is not miscible with the ethanol/perfume mixture.

The rheological profiles at 25° C. (at a shear rate of 10 s$^{-1}$) of the oils tested show a population separation for a viscosity of 10 mPa·s. Thus, the study's MCT and grapeseed oil have a viscosity above this limit. In addition, the MCT and grapeseed oil have spreading values within the "medium"

range, which explains their oiliness on the skin. Finally, these two oils show the lowest evaporations at 70° C. at 210 seconds.

After these various tests, the best lipophilic solvents compatible with the extrusion operation and offering decent olfactory performance without greasiness on the skin are thus esters such as IPM, coco-caprylate, isoadipate, and low-viscosity dimethicones such as octamethyltrisiloxane. It is these esters that are tested below in co-extrusion with various perfumes. Tests with various perfume concentrations are also conducted.

Capsules According to the Invention

The capsules are manufactured by a co-extrusion operation, as described in patent EP513603. The general procedure for preparing the capsules is described below. The external aqueous phase of the gellable mixture and the internal oil phase of the core are individually pumped through a set of immersed coaxial nozzles so as to form a concentric composite stream which separates into discrete concentric drops under the effect of vibrational energy The composition (mass percent) of the capsule shell (gellable mixture) is given in table 5.

TABLE 5

|  | wet capsule | dry capsule |
| --- | --- | --- |
| sorbitol | 1.5% | 20.3% |
| citric acid | 0.2% | 2.7% |
| carrageenan | 4.0% | 54.2% |
| soda | 0.2% | 2.4% |
| gellan gum | 1.5% | 20.3% |
| process water | 92.6% | |
| Total | 100.0% | 100.0% |

Composition of the capsule shell (mass percents)

The composition of the lipophilic core (in mass percents) in different lipophilic mixtures for each sample of capsules is detailed in Table 6. The oils tested with perfume A at 20% are MCT, IPM, isoadipate, and coco-caprylate. Extrusion with perfume A at higher concentration (40%) is tested with coco-caprylate. Finally, extrusion with perfume B at 20% is carried out with coco-caprylate.

All the capsules could be created. The size (mm), hardness (kg), and elasticity (%) values of the associated capsules are also presented in Table 6.

TABLE 6

|  | Sample 1 | Sample 2 | Sample 3 | Sample 4 | Sample 5 | Sample 6 |
| --- | --- | --- | --- | --- | --- | --- |
| COMPOSITION OF LIPOPHILIC MIXTURES (capsule core) | | | | | | |
| Perfume A | 20% | 20% | 20% | 20% | 40% | |
| Perfume B | | | | | | 20% |
| Ethanol | 3% | 3% | 3% | 5% | 3% | 5% |
| MCT | 77% | | | | | |
| IPM | | 77% | | | | |
| Isoadipate | | | 77% | | | |
| Coco-caprylate | | | | 75% | 77% | 75% |
| PHYSICAL CHARACTERIZATION OF ASSOCIATED CAPSULES | | | | | | |
| size (mm) | 3.48 | 3.48 | 3.45 | 3.53 | 3.56 | 3.57 |
| hardness (kg) | 1.613 | 1.516 | 1.629 | 1.409 | 1.427 | 1.260 |
| elasticity (%) | 38% | 34% | 44% | 35% | 39% | 36% |

Composition of the lipophilic mixtures introduced during co-extrusion (mass percents) and physical characteristics of capsules obtained applied to it. The discharge from the set of coaxial nozzles is immersed in a carrier fluid (e.g. MCT), which is at a temperature below the gelation temperature of the gellable mixture. The gellable mixture is thus cooled and forms the hydrated core-shell portion of the capsule. The capsules thus formed are then collected and centrifuged to eliminate most of the residual MCT. The centrifuged capsules and a possible portion of the desiccant (e.g. starch) are mixed, then air dried in an rotary dryer at 40° C. The dried capsules are collected and sieved. The dried breakable capsules, prepared according to embodiments of the invention, have a homogeneous and smooth appearance, and are spherical or substantially spherical (as measured by the average ratio between the width and length of the microcapsules). In one embodiment, the dried breakable capsules also have a texture profile which allows breaking these capsules between two fingers.

In conclusion, an oil miscible with a mixture of fine perfumery perfume and ethanol having a specific gravity between 0.82 and 0.99 makes it possible to produce perfumed capsules whose size is between 3.5 and 4.5 mm; whose hardness is between 0.5 and 2.5 kg; and whose elasticity (expressed as the deformation percentage at break) is between 30 and 50%. However, in order to obtain good evaporation and a high spreading value, esters (such as IPM, isoadipate, and coco-caprylate) and silicones (such as octamethyltrisiloxane) are to be preferred.

Table 7 below allows comparing the volumes of perfume (plus solvent) delivered by a capsule when the capsule is broken. Knowing that on average one spritz of conventional alcohol-based perfume delivers between 50 and 120 µl, it is shown below that a single 5 mm capsule loaded to 90% can deliver 60 µl of perfume, which is advantageous.

TABLE 7

| Capsule diameter | 3.00 mm | 3.20 mm | 3.50 mm | 4.00 mm | 4.10 mm | 4.20 mm | 4.50 mm | 4.75 mm | 5.00 mm |
|---|---|---|---|---|---|---|---|---|---|
| Load of capsule core (w/w) | 85.0% | 86.0% | 87.0% | 88.0% | 80.5% | 88.5% | 89.0% | 89.5% | 90.0% |
| Volume of capsule core (µl) | 12.5 | 15.3 | 20.2 | 30.4 | 30.5 | 35.3 | 43.7 | 51.6 | 60.4 |
| Average weight per capsule | 14 mg | 17 mg | 22 mg | 32 mg | 35 mg | 37 mg | 46 mg | 54 mg | 63 mg |
| Thickness of capsule film | 61 µm | 60 µm | 61 µm | 64 µm | 111 µm | 64 µm | 66 µm | 66 µm | 66 µm |

Physical characteristics of capsules obtained

The invention claimed is:

1. A seamless core-shell capsule for fragrancing a user, the shell comprising at least one hydrocolloid, the core comprising at least one fragrancing agent and at least one lipophilic solvent, wherein said shell is breakable, and the core comprises from 15 to 40% by weight of fragrancing agents relative to the total weight of the core and from 60 to 85% by weight of a non-glyceride lipophilic solvent relative to the total weight of the core, said solvent being miscible with ethanol and having:

a viscosity of less than 10 mPa·s as measured at a temperature of 25° C. and at a shear rate of 10 s$^{-1}$;

a specific gravity of between 0.82 and 0.99; and a spreading value greater than 850 mm$^2$/10 min.

2. The capsule according to claim 1, wherein the solvent is selected from the group consisting of isoadipate, coco-caprylate, isopropyl myristate, and dimethicone 1 cSt.

3. The capsule according to claim 1, wherein the solvent represents between 70 and 80% by weight relative to the weight of the capsule core.

4. The capsule according to claim 1, wherein the capsule has a hardness of between 0.5 and 2.5 kg.

5. The capsule according to claim 1, wherein the shell comprises at least one hydrocolloid selected among gellan gum, gelatin, collagen, alginates, carrageenans, agar-agar, chitosan and its derivatives, pectins, gum arabic, ghatti gum, pullulan gum, mannan gum, or modified starches.

6. The capsule according to claim 5, wherein the hydrocolloid is gellan gum.

7. The capsule according to claim 5, wherein the hydrocolloid is selected from the carrageenans.

8. The capsule according to claim 1, wherein the capsule has a diameter of between 2 and 10 mm.

9. The capsule according to claim 1, wherein the thickness of the capsule shell is between 10 and 500 µm.

10. The capsule according to claim 1, wherein, when it is broken, the perfumed composition does not leave a greasy feeling after application to the skin.

11. A method for manufacturing a breakable capsule comprising a shell and a core, for fragrancing a user, comprising:

(A) co-extrusion of a hydrophilic external liquid phase and a lipophilic internal liquid phase, the external liquid phase comprising from 4 to 95% by weight of a hydrocolloid relative to the dry weight of said external phase, the internal liquid phase comprising from 15 to 40% by weight of fragrancing agents relative to the total weight of the core, from 0 to 10% by weight of ethanol relative to the total weight of the core, and from 60 to 85% by weight of a non-glyceride lipophilic solvent relative to the total weight of the core, said solvent being miscible with ethanol and having:

a viscosity of less than 10 mPa·s as measured at a temperature of 25° C. and at a shear rate of 10 s$^{-1}$;

a specific gravity of between 0.82 and 0.99; and a spreading value greater than 850 mm$^2$/10 min;

(B) solidification and/or gelation of the surface of the capsules thus obtained, by immersion in a cold bath at a temperature of between 1° and 20° C.;

(C) drying the capsules; and (D) collecting the capsules.

12. A method for fragrancing a user, said method comprising:

gripping the capsule according to claim 1, between two of the user's fingers;

rupturing said capsule by the action of a pressure enabling said capsule to be broken between the two fingers; and applying oily perfumed composition contained in the capsule to the skin and/or clothing.

13. The method according to claim 12, wherein the oily perfumed composition does not leave a greasy feeling on the skin.

14. A seamless core-shell capsule for fragrancing a user, the shell comprising at least one hydrocolloid, the core comprising at least one fragrancing agent and coco-caprylate, wherein said shell is breakable, and the core comprises from 15 to 40% by weight of fragrancing agents relative to the total weight of the core and from 60 to 85% by weight of coco-caprylate relative to the total weight of the core, said solvent being miscible with ethanol and having:

a viscosity of less than 10 mPa·s as measured at a temperature of 25° C. and at a shear rate of 10 s$^{-1}$;

a specific gravity of between 0.82 and 0.99; and a spreading value greater than 850 mm$^2$/10 min.

\* \* \* \* \*